United States Patent
Bonrath et al.

(10) Patent No.: US 12,410,117 B2
(45) Date of Patent: Sep. 9, 2025

(54) PROCESS FOR PRODUCTION OF VITAMIN A

(71) Applicant: DSM IP ASSETS B.V., Heerlen (NL)

(72) Inventors: Werner Bonrath, Kaiseraugst (CH); Marc-André Mueller, Kaiseraugst (CH); Bettina Wuestenberg, Kaiseraugst (CH); Viktor Zimmermann, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 528 days.

(21) Appl. No.: 17/915,453

(22) PCT Filed: Mar. 22, 2021

(86) PCT No.: PCT/EP2021/057243
§ 371 (c)(1),
(2) Date: Sep. 28, 2022

(87) PCT Pub. No.: WO2021/197890
PCT Pub. Date: Oct. 7, 2021

(65) Prior Publication Data
US 2023/0125156 A1   Apr. 27, 2023

(30) Foreign Application Priority Data
Mar. 31, 2020   (EP) .................................. 20167019

(51) Int. Cl.
*C07C 67/08* (2006.01)
*C07C 69/28* (2006.01)

(52) U.S. Cl.
CPC ............. *C07C 67/08* (2013.01); *C07C 69/28* (2013.01); *C07C 2601/16* (2017.05)

(58) Field of Classification Search
USPC ......................................................... 514/552
See application file for complete search history.

(56) References Cited

FOREIGN PATENT DOCUMENTS

| CA | 3082441 A1 | * | 5/2018 | ........... A23L 33/155 |
| CN | 102603588 | | 7/2012 | |
| DE | 10341654 A1 | * | 4/2005 | ............... A61K 8/11 |
| NO | 115841 B | * | 12/1968 | ............. C07C 47/42 |

OTHER PUBLICATIONS

International Search Report and Written Opinion of the ISA for PCT/EP2021/057243, mailed Jun. 11, 2021, 14 pages.
Subramanian et al., "Short Synthetic Route to Retinoids Through Dialkylation of 3-Methyl-3-Suldolene", Tetrahedron Letters, vol. 38, No. 14, Apr. 7, 1997, pp. 2585-2586.
T. Subramanian et al., "Convenient Synthesis of 1,3,6-Triene Systems Through Alkylation of 3-Methyl-3-sulfolene", Synthetic Communications, vol. 27, No. 23, Dec. 22, 1997, pp. 4067-4072.
Desai, S.R. et al., Studies in Alkylation of 3-Methyl-3-Sulfolene and Thermolysis of Resulting 2-Alkyl-3-Sulfolenes: Convenient Synthesis of 1,2-Disubstituted-1,3,Dienes, *Tetrahedron,* vol. 48., No. 3, pp. 481-490 (1992).
Subramanian, T. et al, Convenient Synthesis of Retinol-Related Polyenes Through Hydroxylalkylation of 3-Sulfolenes, *Synthetic Communications*, 31(18), 2787-2793 (2001).

* cited by examiner

*Primary Examiner* — Walter E Webb
(74) *Attorney, Agent, or Firm* — Nixon & Vanderhye, P.C.

(57) ABSTRACT

The present invention relates to a new process for the production of vitamin A and/or its derivatives.

15 Claims, No Drawings

PROCESS FOR PRODUCTION OF VITAMIN A

This application is the U.S. national phase of International Application No. PCT/EP2021/057243 filed Mar. 22, 2021, which designated the U.S. and claims priority to EP patent application No. 20167019.7 filed Mar. 31, 2020, the entire contents of each of which are hereby incorporated by reference.

The present invention relates to a new process for the production of vitamin A and/or its derivatives.

Vitamin A or its derivatives such as Vitamin acetate

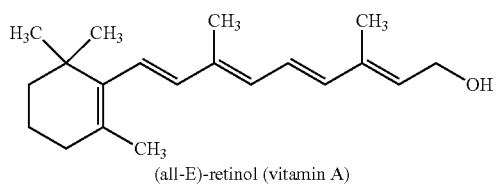 [SMILES: CC1=C(/C=C/C(C)=C/C=C/C(C)=C/CO)C(C)(C)CCC1]

(all-E)-retinol (vitamin A)

is an important ingredient for many applications. Vitamin A plays a role in a variety of functions throughout the body, such as e.g. vision process, gene transcription, immune function, bone metabolism, haematopoiesis, skin and cellular health and antioxidant function.

Due to the importance of vitamin A (and its derivatives) and the complexity of the synthesis thereof, there is always a need for improved processes of production.

The goal of the present invention was to find a new interesting synthesis of vitamin A or its derivates. The aim was achieved by the synthesis as disclosed and described below.

The new synthesis how to obtain vitamin A and/or its derivatives can be seen from the following scheme:

The following schema shows how to produce vitamin A (or derivatives thereof) can be obtained.

wherein
R is H, or —(CO)—(CH$_2$)$_n$CH$_3$, wherein n has a value of 0-14, preferably 0-10, more preferably 0 or 1, most preferably 1, or
R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether.

Therefore the present invention relates to a process (P) for the production of the compound of formula (III)

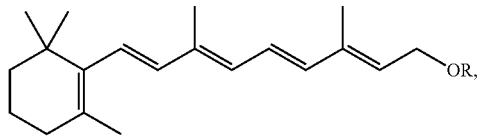

R is H, or —(CO)—(CH$_2$)$_n$CH$_3$, wherein n has a value of 0-14, or
R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether, characterized in that in a
first step (step (i))
a compound of formula (I)

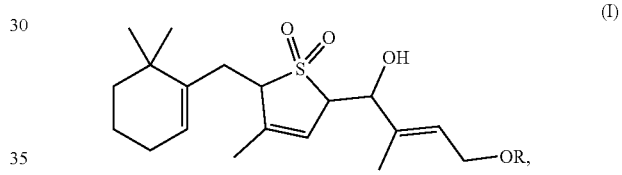

wherein R has the same as defined for the compound of formula (III)

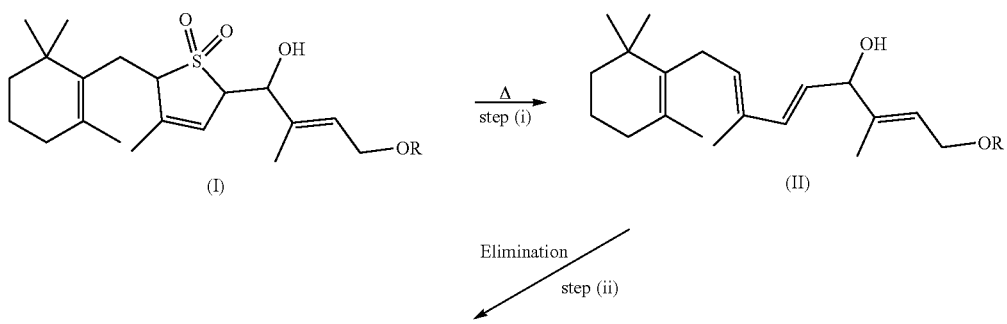

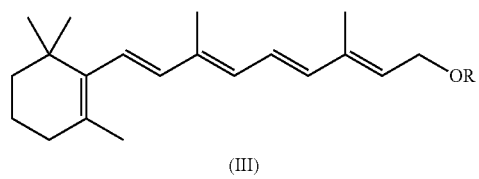

is treated with heat to form a compound of formula (II)

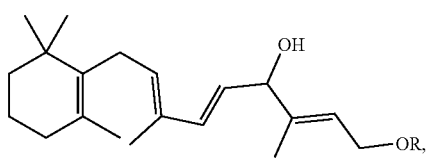
(II)

wherein R has the same as defined for the compound of formula (III),
which is then converted into compound of formula (III) by an elimination reaction (step (ii)).

Therefore the present invention relates to a process (P'), which is process (P), wherein R is H, or —(CO)—(CH₂)ₙCH₃, wherein n has a value of 0-10.

Therefore the present invention relates to a process (P"), which is process (P), wherein R is H, or —(CO)—(CH₂)ₙCH₃, wherein n has a value of 0 or 1.

Therefore the present invention relates to a process (P'''), which is process (P). wherein R is H, or —(CO)—(CH₂)CH₃.

Therefore the present invention relates to a process (P''''), which is process (P). wherein R is —X(C₁₋₄alkyl)₃ or —X(C₆H₅)₃, wherein X is Si or Ge Therefore the present invention relates to a process (P'''''), which is process (P). wherein R is tetrahydro pyrane, isopropylmethyl ether or 2-methoxy-butylether.

The compounds of formula (I), (II) and (III) have several diastereoisomeric forms. Also when not explicitly disclosed all of these forms are all claimed and disclosed by the Markush formulae of these compounds.

The new synthesis comprises two steps (step (i) and step (ii)).

In the following both steps are discussed in more details.
Step (i)
The first step is the ring opening reaction of the compound of formula (I), which is carried out by heating.

The reaction temperature used in step (i) is usually up to 200° C. Usually and preferably the reaction temperature range in step (i) goes from 50° C.-200° C., preferably from 60° C. to 150° C.

Therefore the present invention relates to process (P1), which is process (P), (P'), (P"), (P'''), (P''''') or (P'''''), wherein the reaction temperature in step (i) is up to 200° C.

Therefore the present invention relates to process (P1'), which is process (P), (P'), (P"), (P'''), (P'''') or (P'''''), wherein the reaction temperature range in step (i) goes from 50° C.-200° C.

Therefore the present invention relates to process (P1"), which is process (P), (P'), (P"), (P'''), (P'''') or (P'''''), wherein the reaction temperature range in step (i) goes from 60° C.-150° C.

Optionally, it is possible to add a nitrogen containing base like DABCO, pyridine, picoline, tertiary amine bases, such as Et₃N, (butyl)₃N and dimethylaminopyridine.

Therefore the present invention relates to a process (P2), which is process (P), (P'), (P"), (P'''), (P''''), (P'''''), (P1') or (P1"), wherein the process according to the present invention is carried out in the presence of a nitrogen containing base.

Therefore the present invention relates to a process (P2'), which is process (P2), wherein the nitrogen containing base is chosen from the group consisting of DABCO, pyridine, picoline, tertiary amine bases.

Therefore the present invention relates to a process (P2"), which is process (P2), wherein the nitrogen containing base is chosen from the group consisting of DABCO, pyridine, picoline, Et₃N, (butyl)₃N and dimethylaminopyridine.

The reaction of step (i) is usually carried out in at least one inert solvent. Usually at least one polar aprotic solvent such as pyridine, toluene, xylene, tetrahydrofuran (THF), methyl THF, or ethers (such as diethylether, 1,4-dioxane, 1,2-dimethoxyethane and crown ethers) may be used.

Therefore the present invention relates to process (P3), which is process (P), (P'), (P"), (P'''), (P''''), (P'''''), (P1), (P1'), (P1"), (P2), (P2') or (P2"), wherein the reaction in step (i) is carried out in at least one inert solvent.

Therefore the present invention relates to process (P3'), which is process (P3), wherein the reaction in step (i) is carried out in at least one inert solvent chosen from the group consisting of pyridine, toluene, xylene, THF, methyl THF, or ethers.

Therefore the present invention relates to process (P3"), which is process (P3), wherein the reaction in step (i) is carried out in at least one inert solvent chosen from the group consisting of pyridine, toluene, xylene, THF, methyl THF, diethylether, 1,4-dioxane, 1,2-dimethoxyethane and crown ethers.

The process of step (i) can be carried at atmospheric pressure, as well as under increased pressure or under reduced pressure.

Therefore the present invention relates to process (P4), which is process (P), (P'), (P"), (P'''), (P''''), (P'''''), (P1), (P1'), (P1"), (P2), (P2'), (P2"), (P3), (P3') or (P3"), wherein the reaction in step (i) is carried out at atmospheric pressure.

Therefore the present invention relates to process (P4'), which is process (P), (P'), (P"), (P'''), (P''''), (P'''''), (P1), (P1'), (P1"), (P2), (P2'), (P3), (P3') or (P3"), wherein the reaction in step (i) is carried out under increased pressure.

Therefore the present invention relates to process (P4"), which is process (P), (P'), (P"), (P'''), (P''''), (P'''''), (P1), (P1'), (P1"), (P2), (P2'), (P3) or (P3'), wherein the reaction in step (i) is carried under reduced pressure.

The reaction product obtained in step (i) (compounds of formula (II))

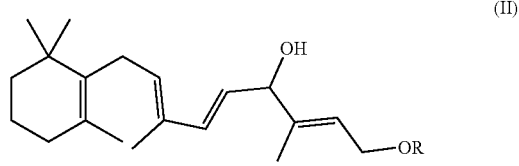
(II)

wherein R has the same as defined for the compound of formula (III) above can be isolated.

The compounds of formula (II) are new.

Therefore the present invention relates to the compounds of formula (II)

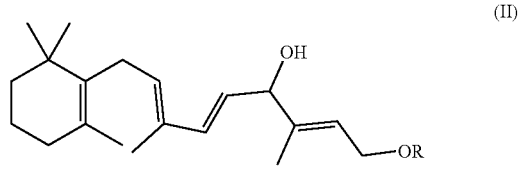
(II)

wherein

R is H, or —(CO)—(CH$_2$)$_n$CH$_3$, wherein n has a value of 0-14, or

R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether.

Therefore the present invention relates to the compounds of formula (II)

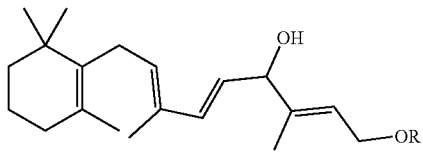

(II)

wherein

R is H, or —(CO)—(CH$_2$)$_n$CH$_3$, wherein n has a value of 0-10, or

R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether.

Therefore the present invention relates to the compounds of formula (II)

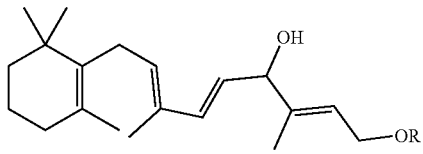

(II)

wherein

R is H, or —(CO)—(CH$_2$)$_n$CH$_3$, wherein n is 0 or 1, or

R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether.

Therefore the present invention relates to the compounds of formula (II)

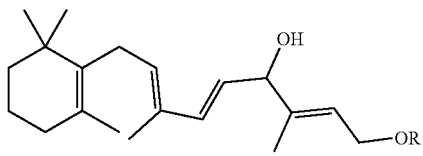

(II)

wherein

R is H, or —(CO)—(CH$_2$) CH$_3$, or

R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether.

Preferred compounds are the one of formula (IIa) and (IIb)

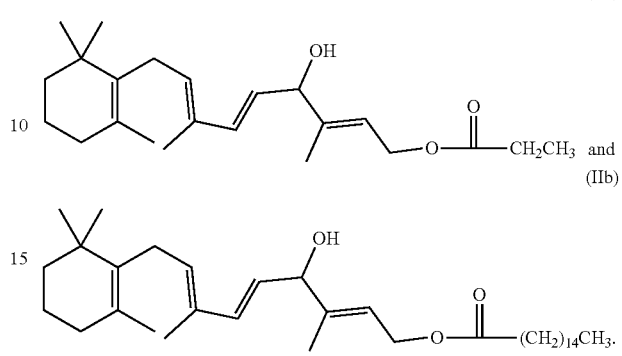

(IIa) and (IIb)

Therefore the present invention also relates to the compound of formula (IIa) and the compound of formula (IIb)

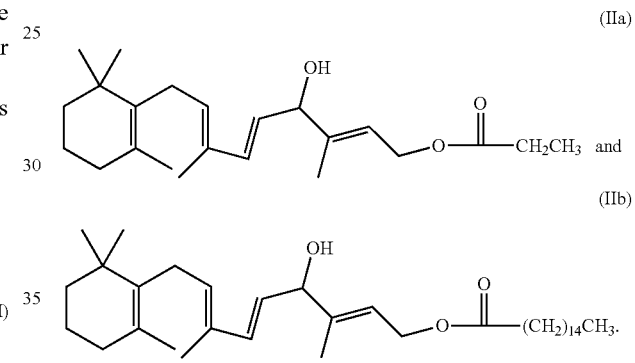

(IIa) and (IIb)

Step (ii)

The second step is an elimination reaction, which leads to the compound of formula (III).

Step (ii) is usually carried out at elevated temperatures.

The reaction temperature used in step (ii) is usually up to 200° C. Usually and preferably the reaction temperature range in step (ii) goes from 50° C.-200° C., preferably from 60° C. to 150° C.

Therefore the present invention relates to process (P5), which is process (P), (P'), (P''), (P'''), (P''''), (P'''''), (P1), (P1'), (P1''), (P2), (P2'), (P3), (P3'), (P4), (P4') or (P4''), wherein the reaction temperature in step (ii) is up to 200° C.

Therefore the present invention relates to process (P5'), which is process (P5), wherein the reaction temperature range in step (ii) goes from 50° C.-200° C.

Therefore the present invention relates to process (P5''), which is process (P5), wherein the reaction temperature range in step (ii) goes from 60° C.-150° C.

The reaction of step (ii) is usually carried out in at least one inert solvent. Usually at least one polar aprotic solvent such as pyridine, toluene, xylene, THF, methyl THF, or ethers (such as diethylether, 1,4-dioxane, 1,2-dimethoxyethane and crown ethers).

Therefore the present invention relates to process (P6), which is process (P), (P'), (P''), (P'''), (P''''), (P'''''), (P1), (P1'), (P1''), (P2), (P2'), (P3), (P3'), (P4), (P4'), (P4''), (P5), (P5') or (P5''), wherein the reaction in step (ii) is carried out in at least one inert solvent.

Therefore the present invention relates to process (P6'), which is process (P6), wherein the reaction in step (ii) is carried out in at least one inert solvent chosen from the group consisting of pyridine, toluene, xylene, THF, methyl THF, or ethers.

Therefore the present invention relates to process (P6″), which is process (P6), wherein the reaction in step (ii) is carried out in at least one inert solvent chosen from the group consisting of pyridine, toluene, xylene, THF, methyl THF, diethylether, 1,4-dioxane, 1,2-dimethoxyethane and crown ethers.

The process of step (ii) can be carried at atmospheric pressure, or under increased pressure or under reduced pressure.

Therefore the present invention relates to process (P7), which is process (P), (P′), (P″), (P‴), (P″″), (P‴″), (P1), (P1′), (P1″), (P2), (P2′), (P3), (P3′), (P4), (P4′), (P4″), (P5), (P5′), (P6), (P6′) or (P6″), wherein the reaction in step (i) is carried out at atmospheric pressure.

Therefore the present invention relates to process (P7′), which is process (P), (P′), (P″), (P‴), (P″″), (P‴″), (P1), (P1′), (P1″), (P2), (P2′), (P3), (P3′), (P4), (P4′), (P4″), (P5), (P5′), (P6), (P6′) or (P6″), wherein the reaction in step (i) is carried out under increased pressure.

Therefore the present invention relates to process (P7″), which is process (P), (P′), (P″), (P‴), (P″″), (P‴″), (P1), (P1′), (P1″), (P2), (P2′), (P3), (P3′), (P4), (P4′), (P4″), (P5), (P5′), (P6), (P6′) or (P6″), wherein the reaction in step (i) is carried out under reduced pressure.

As a preferred embodiment, step (i) and step (ii) are carried as a one pot reaction using the same reaction conditions without isolating the reaction product of step (i).

Both steps can be carried out continuously or discontinuously.

Therefore the present invention relates to process of the production of a compound of formula (III), wherein for step (i) and for step (ii) the same solvent is used, the same temperature and the same pressure are applied.

This can be seen as an one step reaction.

The starting material (compound of formula (I)) can be produced according to the method described as follows:
the compound of formula (I)

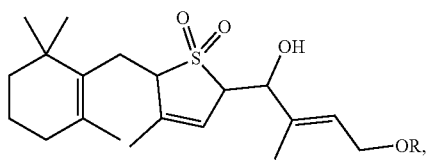

wherein
R is H, or —(CO)—(CH$_2$)$_n$CH$_3$, wherein n has a value of 0-14, preferably 0-10, more preferably 0 or 1, most preferably 1, or
R is —X(C$_{1-4}$alkyl)$_3$ or —X(C$_6$H$_5$)$_3$, wherein X is Si or Ge or R is tetrahydro pyrane, isopropylmethyl ether or 2-methoxy-butylether,
is produced by using the compound of formula (IV)

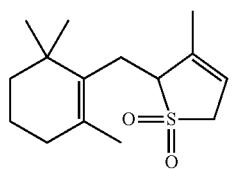

as starting material, which is reacted with a compound of formula (V)

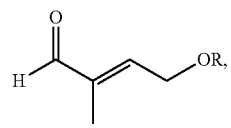

wherein R has the same meanings as defined for the compound of formula (I).

It is known from the prior art how to obtain the compounds of formula (IV) (e. g. from Desai et al. Tetrahedron, 1992, 48, 481-490 or from Kienzle et al. Helvetica Chimica Acta, 1975, 58, 27-40).

The process to produce the compound of formula (I) is usually carried out in the presence of a strong base such as Schlesinger base, 2,2,6,6-tetramethyl piperidine, lithium diisopropylamide, n-butyllithium, hexyllithium, tert.-butyl lithium, sec-butyllithium, metal amide (with metals such as Na, K and Cs), lithium hexamethyldisilazane, metal hydride (with metals such as Na, Mg, K and Cs), metal hydroxide (with metals such as Na, K and Cs), metal alkoxide (with metals such Na, K and Cs) or sodium hexamethyl-disilazane The process to produce the compound of formula (I) is usually carried out in an inert solvent. Preferably the solvent is a polar aprotic solvent. More preferably the solvent is chosen form the group consisting of pyridine, toluene, xylene, THF, methyl THF, or ethers (such as diethylether, 1,4-dioxane, 1,2-dimethoxyethane and crown ethers).

It is also possible to have a mixture of solvents, wherein one solvent can also be a nonpolar solvent (such as heptane, n-pentane, and other hydrocarbones).

The process to produce the compound of formula (I) is usually carried out at low temperature. Usually a temperature range of from −100° C. to 25° C., preferably at a temperature range of from −95° C. to 5° C.

The starting material to produce the compound of formula (I), which are the compounds of formula (IV) and of formula (V) can be used in equimolar amounts. But it is also possible to use an excess of one of the starting material. Usually the equimolar ratio of the compound of formula (IV) to the compound of formula (V) goes from 1:2 to 2:1.

The following example serve to illustrate the invention. The temperature is given in ° C. and all percentages are related to the weight.

EXAMPLES

Example 1: Preparation of (2E,5E,7E)-4-hydroxy-3, 7-dimethyl-9-(2,6,6-trimethylcyclohex-1-en-1-yl) nona-2,5,7-trien-1-yl acetate (Compound of Formula (II))

(E)-4-hydroxy-3-methyl-4-(4-methyl-1,1-dioxido-5-((2, 6,6-trimethylcyclohex-1-en-1-yl)methyl)-2,5-dihydrothiophen-2-yl)but-2-en-1-yl acetate [I] (55 mg, 0.13 mmol; 1.0 eq) and pyridine (3.0 mL) were placed in a dried two necked round bottom flask equipped with a magnetic stirrer and condenser under an argon atmosphere. The reaction mixture was heated to 100° C. for 5 h. All volatiles were evaporated under reduced pressure (50° C., 5 mbar) to obtain the product (43 mg), yield=82%.

Example 2: Synthesis of Vitamin a Derivate Retinyl Acetate (E)-4-hydroxy-3-methyl-4-(4-methyl-1,1-dioxido-5-((2,6,6-trimethylcyclohex-1-en-1-yl)methyl)-2,5-dihydrothiophen-2-yl)but-2-en-1-yl acetate (product obtained from Example 1) (263 mg, 0.6 mmol; 1.0 eq) and dry toluene (5.0 mL) were placed in a dried two necked round bottom flask equipped with a magnetic stirrer and condenser under an argon atmosphere. The reaction mixture was heated to reflux for 2 h. All volatiles were evaporated under reduced pressure (40° C., 5 mbar) to obtain the product in a yield of 71%.

Example 3: Preparation of Retinyl Propionate

3-Methyl-2-((2,6,6-trimethylcyclohex-1-en-1-yl)methyl)-2,5-dihydrothiophene 1,1-dioxide (310 mg, 1.1 mmol; 1.0 eq), (E)-3-methyl-4-oxobut-2-en-1-yl propionate (190 mg, 1.2 mmol; 1.1 eq) and dry toluene (2.0 mL) were placed in a dried two necked round bottom flask under an argon atmosphere. The reaction mixture was cooled to −76° C. Lithium diidopropylamide (1.2 mL, 1.2 mmol, 1.1 eq, 1 M in tetrahydrofuran/hexane, d=0.719 g/mL) was added over a period of 7 min. The reaction mixture was stirred at −76° C. for 7 min. Subsequently the cooling bath was removed and half saturated ammonium chloride solution (5 mL) was added. The reaction mixture was diluted and extracted with toluene (10 mL). The aqueous layer was separated and extracted with toluene (10 mL). The organic layers were washed with water (2×10 mL) and saturated sodium chloride solution (1×10 mL). The combined organic layers were filtered over a plug of cotton wool. All volatiles were evaporated at 40° C. (5 mbar).

The residue placed in a dried two necked round bottom flask and dissolved in toluene (5 mL) with a magnetic stirrer, condenser under an argon atmosphere. The reaction mixture was heated to reflux for 2 h. All volatiles were evaporated under reduced pressure (50° C., 5 mbar) to obtain the product (399 mg), yield=52%.

Example 4

3-Methyl-2-((2,6,6-trimethylcyclohex-1-en-1-yl)methyl)-2,5-dihydrothiophene 1,1-dioxide (308 mg, 1.1 mmol; 1.0 eq), (E)-3-methyl-4-oxobut-2-en-1-yl acetate (161 mg, 1.1 mmol; 1.0 eq) and dry toluene (2.0 mL) were placed in a dried two necked round bottom flask equipped with a magnetic stirrer under an argon atmosphere. The reaction mixture was cooled to −76° C. Lithium diidopropylamide (1.2 mL, 1.2 mmol, 1.1 eq, 1 M in tetrahydrofuran/hexane, d=0.719 g/mL) was added dropwise over a period of 8 min. The reaction was stirred at −76° C. for 7 min. Subsequently the cooling bath was removed and half saturated ammonium chloride solution (5 mL) was added. The reaction mixture was diluted with toluene (10 mL). The aqueous layer was separated and extracted with toluene (10 mL). The organic layers were washed with water (2×10 mL) and saturated sodium chloride solution (10 mL). The combined organic layers were filtered over a plug of cotton wool. All volatiles were evaporated at 40° C. (5 mbar).

The residue was placed in a dried two necked round bottom flask and dissolved in toluene (5 mL) with a magnetic stirrer under an argon atmosphere. The reaction mixture was heated to reflux for 1 h. All volatiles were evaporated under reduced pressure (40° C., 5 mbar) purification afforded the product in 34% yield.

The invention claimed is:

1. A process for the production of the compound of formula (III)

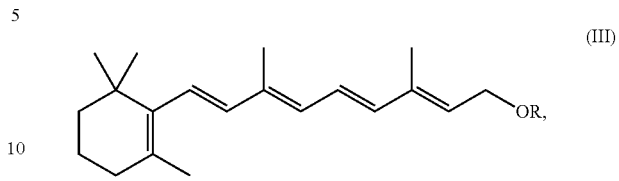

wherein R is H or —(CO)—(CH$_2$)$_n$CH$_3$, wherein n has a value of 0-14, or

R is —X(C$_{1-4}$alkyl)$_3$ or —X(C$_6$H$_5$)$_3$, wherein X is Si or Ge, or

R is tetrahydro pyrane, isopropylmethyl ether or 2-methoxy-butylether, wherein the process comprises:

(i) conducting a first step of treating a compound of formula (I):

(I)

with heat to form a compound of formula (II):

(II)

wherein R in the formulas (I) and (II) has the same meaning as defined for the compound of formula (III), and then (II) conducting an elimination reaction in a second step to convert the compound of formula (II) into the compound of formula (III).

2. The process according to claim 1, wherein the first step (i) is conducted at a reaction temperature of up to 200° C.

3. The process according to claim 2, wherein the reaction temperature of the first step (i) is from 50° C.-200° C.

4. The process according to claim 2, wherein the reaction temperature of the first step (i) is from 60° C.-150° C.

5. The process according to claim 1, wherein the first step (i) is carried out in at least one inert solvent.

6. The process according to claim 5, wherein the at least one inert solvent is selected from the group consisting of pyridine, toluene, xylene, tetrahydrofuran (THF), methyl THF and ethers.

7. The process according to claim 1, wherein the first step (i) is conducted at atmospheric pressure.

8. The process according to claim 1, wherein the second step (ii) is conducted at a reaction temperature of up to 200° C.

9. The process according to claim 8, wherein the reaction temperature of the second step (ii) is from 50° C.-200° C.

10. The process according to claim 8, wherein the reaction temperature of the second step (ii) is from 60° C.-150° C.

11. The process according to claim 1, wherein the second step (ii) is conducted in at least one inert solvent.

12. The process according to claim 11, wherein the at least one inert solvent is selected from the group consisting of pyridine, toluene, xylene, tetrahydrofuran (THF), methyl THF and ether.

13. The process according to claim 1, wherein the second step (ii) is conducted at atmospheric pressure.

14. The process according to claim 1, wherein the first step (i) and the second step (ii) are conducted as a one pot reaction using the same reaction conditions without isolating the reaction of the first reaction step (i).

15. A compound of formula (II):

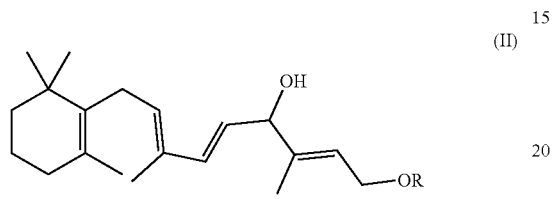

(II)

wherein

R is H or —(CO)—(CH$_2$)$_n$CH$_3$, wherein n has a value of 0-14, or

R is —X(C$_{1-4}$alkyl)$_3$ or —X(C$_6$H$_5$)$_3$, wherein X is Si or Ge, or R is tetrahydro pyrane, isopropylmethyl ether or 2-methoxy-butylether.

* * * * *